(12) United States Patent
Odedra et al.

(10) Patent No.: US 8,927,748 B2
(45) Date of Patent: Jan. 6, 2015

(54) ALKYL-SUBSTITUTED ALLYL CARBONYL METAL COMPLEXES AND USE THEREOF FOR PREPARING DIELECTRIC THIN FILMS

(75) Inventors: Rajesh Odedra, Victoria (CA); Neil Boag, Mytholmroyd W. Yorkshire (GB); Jeff Anthis, Haverhill, MA (US); Ravi Kanjolia, North Andover, MA (US); Mark Saly, North Andover, MA (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 101 days.

(21) Appl. No.: 13/569,906

(22) Filed: Aug. 8, 2012

(65) Prior Publication Data

US 2013/0041170 A1 Feb. 14, 2013

Related U.S. Application Data

(60) Provisional application No. 61/522,985, filed on Aug. 12, 2011.

(51) Int. Cl.
*C07F 13/00* (2006.01)
*C23C 16/00* (2006.01)
*C23C 16/18* (2006.01)
*C23C 16/40* (2006.01)
*C23C 16/455* (2006.01)
*H01L 21/02* (2006.01)
*H01L 21/285* (2006.01)
*H01L 21/768* (2006.01)

(52) U.S. Cl.
CPC ........... *C07F 13/00* (2013.01); *C23C 16/18* (2013.01); *C23C 16/40* (2013.01); *C23C 16/45553* (2013.01); *H01L 21/02142* (2013.01); *H01L 21/02175* (2013.01); *H01L 21/02271* (2013.01); *H01L 21/0228* (2013.01); *H01L 21/28562* (2013.01); *H01L 21/76841* (2013.01)
USPC ......................... 556/46; 427/255.28; 427/569

(58) Field of Classification Search
USPC ................................ 556/46; 427/255.28, 569
See application file for complete search history.

(56) References Cited

U.S. PATENT DOCUMENTS

| 4,388,021 A | 6/1983 | Weiss |
| 4,680,953 A | 7/1987 | Fabris |
| 4,988,159 A | 1/1991 | Turner et al. |
| 6,541,067 B1 | 4/2003 | Marsh et al. |
| 6,698,728 B1 | 3/2004 | Ravetz et al. ............... 261/121.1 |
| 7,282,119 B2 | 10/2007 | Odedra et al. .................. 203/29 |

(Continued)

FOREIGN PATENT DOCUMENTS

| JP | 2006-328526 A | 12/2006 | |
| TW | 200540291 | 12/2005 | ............... C23C 16/34 |

(Continued)

OTHER PUBLICATIONS

Palmer et al., Journal of American Chemical Society, vol. 107, No. 11, pp. 3122-3129 (1985).*

(Continued)

*Primary Examiner* — Porfirio Nazario Gonzalez
(74) *Attorney, Agent, or Firm* — Harness, Dickey & Pierce, P.L.C.

(57) ABSTRACT

Organometallic complexes and use thereof in thin film deposition, such as CVD and ALD are provided herein. The organometallic complexes are (alkyl-substituted $\eta^3$-allyl)(carbonyl)metal complexes.

26 Claims, 5 Drawing Sheets

(56) References Cited

U.S. PATENT DOCUMENTS

| | | | |
|---|---|---|---|
| 7,419,698 B2 | 9/2008 | Jones | 427/248.1 |
| 7,927,661 B2 | 4/2011 | Jones | 427/255.31 |
| 8,039,062 B2 | 10/2011 | Heys et al. | 427/585 |
| 8,221,852 B2 | 7/2012 | Heys et al. | 427/569 |
| 2003/0096468 A1 | 5/2003 | Soininen et al. | |
| 2007/0202254 A1 | 8/2007 | Ganguli et al. | 427/252 |
| 2008/0132050 A1 | 6/2008 | Lavoie | 438/584 |
| 2008/0251016 A1 | 10/2008 | Cunning et al. | 118/722 |
| 2008/0282970 A1 | 11/2008 | Heys et al. | 117/104 |
| 2009/0022891 A1 | 1/2009 | Sakai et al. | |
| 2010/0256406 A1 | 10/2010 | Kanjolia et al. | 556/136 |
| 2010/0261350 A1 | 10/2010 | Kanjolia et al. | 438/681 |
| 2011/0021803 A1 | 1/2011 | Jin et al. | 558/150 |
| 2011/0151227 A1 | 6/2011 | Chalker et al. | 428/220 |
| 2011/0165401 A1 | 7/2011 | Chalker et al. | 428/220 |
| 2011/0165780 A1 | 7/2011 | Kanjolia et al. | 438/785 |
| 2011/0174416 A1 | 7/2011 | Hubsch et al. | |
| 2011/0184156 A1 | 7/2011 | Jones | 534/15 |
| 2012/0177845 A1 | 7/2012 | Odedra et al. | 427/569 |
| 2012/0178266 A1 | 7/2012 | Heys et al. | 438/785 |
| 2013/0052368 A1 | 2/2013 | Rushworth et al. | 427/569 |
| 2013/0196065 A1 | 8/2013 | Heys et al. | |

FOREIGN PATENT DOCUMENTS

| | | | |
|---|---|---|---|
| TW | 200746268 | 12/2007 | |
| WO | WO 2006/131751 | 12/2006 | C23C 16/18 |
| WO | WO 2007/057631 | 5/2007 | C23C 16/448 |
| WO | WO 2009/015270 | 1/2009 | C07F 15/00 |
| WO | WO 2009/015271 | 1/2009 | C07F 15/00 |
| WO | WO 2009/036045 | 3/2009 | C23C 16/455 |
| WO | WO 2009/036046 | 3/2009 | C23C 16/455 |
| WO | WO 2009/086263 | 7/2009 | C23C 16/40 |
| WO | WO 2009/117583 | 9/2009 | C07F 9/09 |
| WO | WO 2009/143452 | 11/2009 | C23C 16/40 |
| WO | WO 2009/143456 | 11/2009 | C23C 6/455 |
| WO | WO 2009/143458 | 11/2009 | C23C 16/40 |
| WO | WO 2009/143460 | 11/2009 | C23C 16/40 |
| WO | WO 2009/146423 | 12/2009 | C23C 16/16 |
| WO | WO 2009/155507 | 12/2009 | C23C 16/18 |
| WO | WO 2009/155520 | 12/2009 | C23C 16/18 |
| WO | WO 2011/011299 | 1/2011 | C23C 16/40 |
| WO | WO 2011/017068 | 2/2011 | C07F 15/06 |
| WO | WO 2011/053505 | 5/2011 | C23C 16/448 |
| WO | WO 2011/097100 | 8/2011 | B01B 1/00 |
| WO | WO 2011/112413 | 9/2011 | C23C 16/00 |
| WO | WO 2011/115878 | 9/2011 | C23C 16/18 |
| WO | WO 2012/027575 | 3/2012 | C07F 11/00 |
| WO | WO-2013/112383 A1 | 8/2013 | |

OTHER PUBLICATIONS

Abel et al., Angew. Chem. Internat. Edit., vol. 10, No. 5, pp. 339-340 (1971).*

Dickson, R., et al. (1996) "The assessment of some cobalt and cobalt-tellurium complexes for MOCVD applications" Polyhedron, 15(13):2237-2245.

George, S., et al. (1996) "Surface chemistry for atomic layer growth" Journal of Physical Chemistry, 100:13121-13131.

Husebye, S., et al. (1964) "Hydrogen shift in the complex formation between deuterium tetracarbonylcobaltate (-I) and 1,4-Pentadiene" Acta Chemica Scandinavica 18(7):1581-1585.

Pankayatselvan, R., et al. (1990) "Regioselectivity of nucleophilic additions to substituted ($\eta^4$-diene) $Co(CO)_3BF_4$ complexes" Journal of Organometallic Chemistry 384:361-380.

Potter, R., et al. (2005) "Deposition of $HfO_2$, $Gd_2O_3$ and $PrO_x$ by liquid injection ALD techniques" Chemical Vapor Deposition, 11(3):159-169.

International Search Report for PCT/US2010/043300 dated Sep. 17, 2010.

EP Communication for EP Application No. 10738124.6 dated Feb. 11, 2013.

International Preliminary Report on Patentability for International Application No. PCT/US2010/043300 dated Feb. 7, 2012.

Burton, B., et al. (2009) "Atomic layer deposition of MnO using Bis(ethylcyclopentadienyl)manganese and $H_2O$" Thin Solid Films 517:5658-5665.

McClellan, W., et al. (1961) "π-Allyl derivatives of transition metals" π-Allyl Derivatives of Transition Metals, Contribution No. 643 from the Central Research Department, 83:1601-1607.

Nilsen, O., et al. (2003) "Growth of manganese oxide thin films by atomic layer deposition" Thin Solid Films 444:44-51.

Qin, X., et al. (2012) "Thermal chemistry of $Mn_2(CO)_{10}$ during deposition of thin manganese films on silicon oxide and on copper surfaces" J. Vac. Sci. Technol. A 30(1).

Office Action dated Feb. 25, 2014 issued in U.S. Appl. No. 13/388,861.

Office Action dated Feb. 17, 2014 issued in Chinese Application No. 201080041747.1 with English Translation.

Search Report and Written Opinion dated Apr. 15, 2013 issued in Singapore Application No. 201200801-7.

Office Action dated Jul. 10, 2014 issued in U.S. Appl. No. 13/388,861.

Japanese Office Action dated Mar. 4, 2014 issued in Japanese Application No. 2012-523641 with English Translation.

* cited by examiner

ALKYL-SUBSTITUTED ALLYL CARBONYL METAL COMPLEXES AND USE THEREOF FOR PREPARING DIELECTRIC THIN FILMS

CROSS-REFERENCE TO RELATED APPLICATIONS

This application claims the benefit of U.S. Provisional Application Ser. No. 61/522,985 filed Aug. 12, 2011, the disclosure of which is hereby incorporated by reference for all purposes in its entirety as if fully set forth herein.

FIELD OF THE INVENTION

The present invention relates to (alkyl-substituted $\eta^3$-allyl)(carbonyl)metal complexes and methods of preparing thin films by chemical vapor deposition (CVD) or atomic layer deposition (ALD) using such complexes.

BACKGROUND OF THE INVENTION

Various organometallic precursors are used to form thin metal films and a variety of deposition techniques have been employed. These include reactive sputtering, ion-assisted deposition, sol-gel deposition, CVD, and ALD, also known as atomic layer epitaxy. The CVD and ALD processes are increasingly used as they have the advantages of good compositional control, high film uniformity, good control of doping and, significantly, they give excellent conformal step coverage on highly non-planar microelectronics device geometries.

CVD (also referred to as metalorganic CVD or MOCVD) is a chemical process whereby precursors are used to form a thin film on a substrate. In a typical CVD process, the precursors are passed over a substrate (wafer) within a low pressure or ambient pressure reaction chamber. The precursors react and/or decompose on the substrate surface creating a thin film of deposited material. Volatile by-products are removed by gas flow through the reaction chamber. The deposited film thickness can be difficult to control because it depends on coordination of many parameters such as temperature, pressure, gas flow volumes and uniformity, chemical depletion effects and time.

ALD is a common method for the deposition of thin films. It is a self-limiting, sequential, unique film growth technique based on surface reactions that can provide atomic layer-forming control and deposit-conformal thin films of materials provided by precursors onto substrates of varying compositions. In ALD, the precursors are separated during the reaction. The first precursor is passed over the substrate producing a monolayer on the substrate. Any excess unreacted precursor is pumped out of the reaction chamber. A second precursor is then passed over the substrate and reacts with the first precursor, forming a second monolayer of film over the first-formed monolayer of film on the substrate surface. This cycle is repeated to create a film of desired thickness. ALD film growth is self-limited and based on surface reactions, creating uniform depositions that can be controlled at the nanometer-thickness scale.

Dielectric thin films have a variety of important applications, such as nanotechnology and fabrication of semiconductor devices. Examples of such applications include high-refractive index optical coatings, corrosion-protection coatings, photocatalytic self-cleaning glass coatings, biocompatible coatings, dielectric capacitor layers and gate dielectric insulating films in FETs (Field-Effect Transistor), capacitor electrodes, gate electrodes, adhesive diffusion barriers and integrated circuits. Dielectric thin films are also used in microelectronics applications, such as the high-K dielectric oxide for dynamic random access memory (DRAM) applications and the ferroelectric perovskites used in infrared detectors and non-volatile ferroelectric random access memories (NV-FeRAMs). The continual decrease in the size of microelectronics components has increased the need for the use of such dielectric thin films.

Manganese-containing films have found numerous practical applications in areas such as catalysts, batteries, memory devices, displays, sensors, and nano- and microelectronics. In the case of electronic applications, metallic manganese films can act as barriers to prevent diffusion of copper interconnects into underlying silicon dioxide substrate.

Others have reported manganese carbonyl complexes with allyl ligands. See, for example, Palmer G. and Basolo F. *J. Am. Chem. Soc.* 107:3122-3129 (1985). Deposition of certain manganese complexes has also been reported. See, for example: Burton B. B. et al. *Thin Solid Films* 517:5658-5665 (2009); Nilsen O. et al. *Thin Solid Films* 444:44-51 (2003); and Qin X. et al. *J. Vac. Sci. Technol. A.* 30:01 A112-1-01A112-10 (2012).

Current precursors for use in CVD and ALD do not provide the required performance to implement new processes for fabrication of next generation devices, such as semiconductors. For example, improved thermal stability, higher volatility, reduced vapor pressures, increased deposition rates and a high permittivity and/or increased barrier properties are needed.

SUMMARY OF THE INVENTION

In one embodiment, an organometallic complex represented by Formula I is provided:

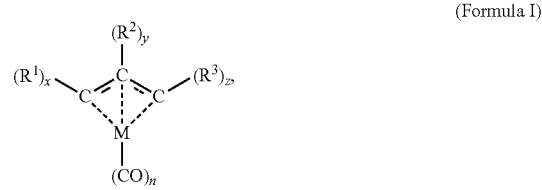

(Formula I)

wherein

M is Ni, V, Nb, Ta, Mn, Re, Rh or Ir;

$R^1$, $R^2$, and $R^3$ are independently $C_1$-$C_8$-alkyl;

x and z are independently zero, 1 or 2;

y is zero or 1; and wherein when M is Ni, then n is 1;

when M is V, Nb or Ta, then n is 5;

when M is Re, then n is 4; and when M is Rh or Ir, then n is 3.

In some such embodiments, the complex represented by Formula I is a manganese complex represented by Formula IA:

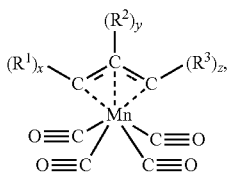

(Formula IA)

wherein
$R^1$, $R^2$, and $R^3$ are independently $C_1$-$C_8$-alkyl;
x and z are independently zero, 1 or 2; and
y is zero or 1.

In another embodiment, an organometallic complex represented by Formula II is provided:

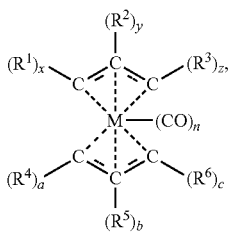

(Formula II)

wherein
M is Ti, Cr, Fe or Ni;
$R^1$, $R^2$, $R^3$, $R^4$, $R^5$, and $R^6$ are independently $C_1$-$C_8$-alkyl;
x, z, a, and c are independently zero, 1, or 2;
y and b are independently zero or 1; and wherein
when M is Ni, then n is zero;
when M is Fe, then n is 2;
when M is Cr, then n is 3; and
when M is Ti, then n is 4.

In another embodiment, an organometallic complex represented by Formula III is provided:

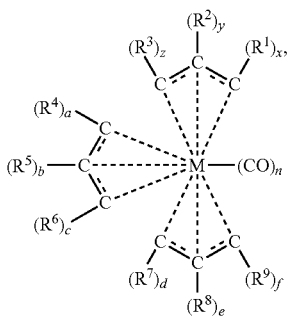

(Formula III)

wherein
M is Mn or V;
$R^1$, $R^2$, $R^3$, $R^4$, $R^5$, $R^6$, $R^7$, $R^8$, and $R^9$ are independently $C_1$-$C_8$-alkyl;
x, z, a, c, d, and f are independently zero, 1, or 2;
y, b, and e are independently zero or 1; and wherein
when M is Mn, then n is 1; and
when M is V, then n is 2.

In another embodiment, an organometallic complex represented by Formula IV is provided:

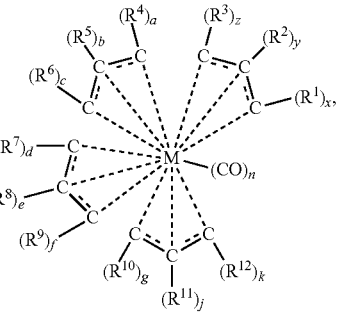

(Formula IV)

wherein
M is Cr or Ti;
$R^1$, $R^2$, $R^3$, $R^4$, $R^5$, $R^6$, $R^7$, $R^8$, $R^9$, $R^{10}$, $R^{11}$, and $R^{12}$ are independently $C_1$-$C_8$-alkyl;
x, z, a, c, d, f, g, and k are independently zero, 1, or 2;
y, b, e, and j are independently zero or 1; and wherein
when M is Cr, then n is zero; and
when M is V, then n is 1.

In another embodiment, an organometallic complex represented by Formula V is provided:

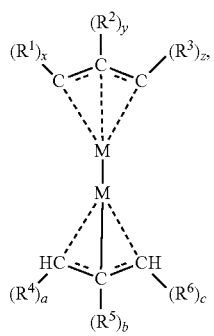

(Formula V)

wherein
M is Ni, Fe, Cr, or Ti;
$R^1$, $R^2$, $R^3$, $R^4$, $R^5$, and $R^6$ are independently $C_1$-$C_8$-alkyl;
x, z, a, and c are independently zero, 1, or 2;
y and b are independently zero or 1; and wherein
when M is Ni, then n is 2;
when M is Fe, then n is 3;
when M is Cr, then n is 4; and
when M is Ti, then n is 5.

In another embodiment, an organometallic complex represented by Formula VI is provided:

$$M(CO)_n \quad \text{(Formula VI)},$$

wherein
M is Fe, Cr, Ti, and Ni; and wherein
when M is Ni, then n is 4;
when M is Fe, then n is 5;
when M is Cr, then n is 6; and
when M is Ti, then n is 7.

Methods for forming metal-containing films by vapor deposition processes, such as CVD and ALD are also provided herein using organometallic complexes according to any of the Formulas above.

Other embodiments, including particular aspects of the embodiments summarized above, will be evident from the detailed description that follows.

DETAILED DESCRIPTION OF THE INVENTION

Figure 1:
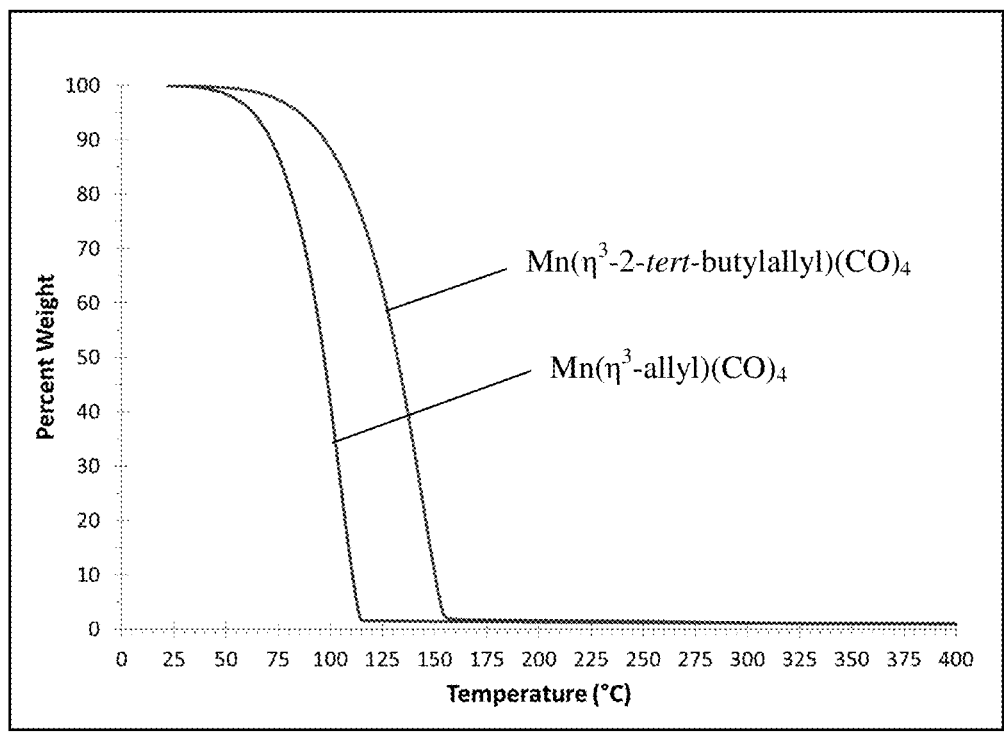
FIG. 1 is a graphical representation of thermal gravimetric analysis (TGA) data demonstrating % weight loss vs. temperature for $Mn(\eta^3\text{-}2\text{-tert-butylallyl})(CO)_4$ and $Mn(\eta^3\text{-allyl})(CO)_4$.

In various aspects of the invention, allyl organometallic complexes, methods of making such complexes and methods of using such complexes to form thin metal-containing films, such as but not limited to, metal, metal-Si, metal-oxide or metal-nitride films, are provided.

The methods of the invention are used to create or grow metal-containing thin films which display high dielectric constants or which act as barrier films. A dielectric thin film as used herein refers to a thin film having a high permittivity.

As used herein, the term "high-ic dielectric" refers to a material, such as a metal-containing film, with a higher dielectric constant ($\kappa$) when compared to silicon dioxide (which has a dielectric constant of about 3.7). Typically, a high-κ dielectric film is used in semiconductor manufacturing processes to replace a silicon dioxide gate dielectric. A high-κdielectric film may be referred to as having a "high-κgate property" when the dielectric film is used as a gate material and has at least a higher dielectric constant than silicon dioxide.

As used herein, the term "relative permittivity" is synonymous with dielectric constant ($\kappa$).

As used herein, the term "precursor" refers to an organometallic molecule, complex and/or compound which is deposited or delivered to or passed over a substrate to form a thin film by a vapor deposition process such as CVD or ALD.

As used herein, the term "vapor deposition process" is used to refer to any type of vapor deposition technique such as CVD or ALD. In various embodiments of the invention, CVD may take the form of conventional (pulsed) CVD, liquid injection CVD or photo-assisted CVD. In other embodiments, ALD may take the form of conventional (pulsed) ALD, liquid injection ALD, photo-assisted ALD, plasma-assisted ALD, or plasma-enhanced ALD.

The allyl and substituted-allyl organometallic complexes of the invention represent substantially improved sources for thin film deposition. For example, the inventors have found that the more bulky substituted-allyl complexes actually reduce vapor pressure and thus are easier to handle. Further, the new complexes have a different volatility which allows for common solvents to be used in their synthesis. This permits a more efficient separation, making it easier to isolate the complex to very high purity.

The targeted deposition temperatures for these complexes, for example about 90° C. to about 200° C., are lower than for other complexes. Access to low-temperature processing makes integration easier as underlying circuitry does not have to withstand such a high thermal budget.

Carbon incorporation should be avoided as it reduces the conductivity of the film and degrades device performance. Without being bound by theory, the inventors propose that the bulky groups substituted on the allyl may decompose via a different mechanism which does not result in as many methyl radicals on the surface. Methyl radicals react to provide very strong metal-carbon bonds, leading to impermissibly high levels of carbon incorporation. The cleaner "leaving" of the organic groups reduces this unwanted reaction and should therefore reduce resistance and improve conductivity of the final films formed.

Further, another advantage of the instant complexes are that they are typically liquid at room temperature, which is beneficial for handling.

Therefore, in a first embodiment, an (alkyl-substituted $\eta^3$-allyl)(carbonyl)metal organometallic complex is provided. The organometallic complex corresponds in structure to Formula I:

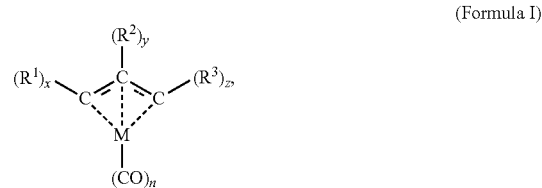

(Formula I)

wherein
M is V, Nb, Ta, Mn, Re, Rh or Ir;
$R^1$, $R^2$, and $R^3$ are independently $C_1$-$C_8$-alkyl;
x and z are independently zero, 1 or 2;
y is zero or 1; and wherein
when M is V, Nb or Ta, then n is 5;
when M is Mn or Re, then n is 4; and
when M is Rh or Ir, then n is 3.

It should be noted that the complexes of the invention, represented by the depiction above, have a resonating double bond in the allyl portion and the allyl portion is $[C_3H_5]$ which is in $\eta^3$-coordination with the metal center. Both of these features are represented by the dashed bonds. When the allyl portion is substituted by one R group, the R group replaces an allylic hydrogen to become $[RC_3H_4]$, when substituted with two R groups it becomes $[R^1R^2C_3H_3]$ where $R^1$ and $R^2$ are the same or different, and so forth.

The term "alkyl" (alone or in combination with another term(s)) refers to a saturated hydrocarbon chain of 1 to about 8 carbon atoms in length, such as, but not limited to, methyl, ethyl, propyl, butyl, pentyl, hexyl, heptyl and octyl. The alkyl group may be straight-chain or branched-chain. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl. Further, as used herein, "Me" refers to methyl, "Et" refers to ethyl, "i-Pr" refers to isopropyl, "t-Bu" refers to tert-butyl, and "Np" refers to neopentyl. It should also be noted that $C_2$ is intended to refer to an ethyl group and not geminal dimethyl groups.

In one embodiment, $R^1$, $R^2$ and $R^3$ are independently $C_1$-$C_8$-alkyl, particularly $C_2$-$C_8$-alkyl, more particularly $C_3$-$C_8$-alkyl, more particularly $C_4$-$C_8$-alkyl, and even more particularly $C_5$-$C_8$-alkyl.

In another particular embodiment, $R^1$, $R^2$ and $R^3$ are independently $C_3$-$C_7$-alkyl, and even more particularly $C_4$-$C_7$-alkyl.

In one embodiment, $R^1$, $R^2$ and/or $R^3$ is propyl. Therefore, $R^1$, $R^2$ and/or $R^3$ may be n-propyl or isopropyl.

In another embodiment, $R^1$, $R^2$ and/or $R^3$ is butyl. $R^1$, $R^2$ and/or $R^3$ may be n-butyl, sec-butyl, isobutyl or tert-butyl. In a particular embodiment, $R^1$, $R^2$ and/or $R^3$ is tert-butyl.

In another embodiment, $R^1$, $R^2$ and/or $R^3$ is pentyl. $R^1$, $R^2$ and/or $R^3$ may be neopentyl, straight-chained, or isopentyl. In a particular embodiment, $R^1$, $R^2$ and/or $R^3$ is neopentyl.

In another embodiment, $R^1$, $R^2$ and/or $R^3$ is hexyl.

In another embodiment, $R^1$, $R^2$ and/or $R^3$ is heptyl.

In another embodiment, $R^1$, $R^2$ and/or $R^3$ is octyl.

As used herein, the variables, x, y and z are used to represent how many particular R substituents are attached to the appropriate carbon.

In one embodiment, x and z are independently zero, 1 or 2.

In one embodiment, y is zero or 1.

In a particular embodiment, x is one and y and z are each zero.

In another particular embodiment, y is one, and x and z are each zero.

In another particular embodiment, at least two of x, y and z are one.

In another particular embodiment, x, y and z are each one.

The center metal can be Mn, Ni, V, Nb, Ta, Re, Rh or Ir. In a particular embodiment, the metal is Mn.

The variable "n" in the complex of Formula I is used to designate how many carbonyl ligands are bonded to the metal center which depends on the valency of the metal used. For example, when M is Ni, then n is 1; when M is V, Nb or Ta, then n is 5; when M is Re or Mn, then n is 4; and when M is Rh or Ir, then n is 3, and so forth.

Other examples are shown in Table 1, below.

TABLE 1

| Ti(allyl)$_{2x}$(CO)$_{7-3x}$ | x = 0, 1, 2 |
|---|---|
| V(allyl)$_{1+2x}$(CO)$_{5-3x}$ | x = 0, 1 |
| Cr(allyl)$_{2x}$(CO)$_{6-3x}$ | x = 0, 1, 2 |
| Mn(allyl)$_{1+2x}$(CO)$_{4-3x}$ | x = 0, 1 |
| Fe(allyl)$_{2x}$(CO)$_{5-3x}$ | x = 0, 1 |
| Ni(allyl)$_{2x}$(CO)$_{4-3x}$ | x = 0, 1 |

In a particular embodiment, the complex represented by Formula I is a manganese complex represented by Formula IA:

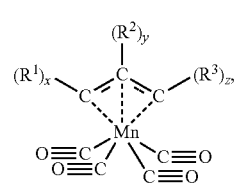
(Formula IA)

wherein
$R^1$, $R^2$, and $R^3$ are independently $C_1$-$C_8$-alkyl;
x and z are independently zero, 1 or 2; and y is zero or 1.

In one such embodiment, $R^1$, $R^2$ and $R^3$ are independently $C_1$-$C_8$-alkyl, particularly $C_2$-$C_8$-alkyl, more particularly $C_3$-$C_8$-alkyl, more particularly $C_4$-$C_8$-alkyl, and even more particularly $C_5$-$C_8$-alkyl.

In one embodiment, at least one of $R^1$, $R^2$, or $R^3$ is $C_5$-$C_8$-alkyl.

In one embodiment, at least one of $R^1$, $R^2$, or $R^3$ is branched $C_5$-$C_8$-alkyl.

In another particular embodiment, $R^1$, $R^2$ and $R^3$ are independently $C_3$-$C_7$-alkyl, and even more particularly $C_4$-$C_7$-alkyl.

In one embodiment, $R^1$, $R^2$ and/or $R^3$ is propyl. Therefore, $R^1$, $R^2$ and/or $R^3$ may be n-propyl or isopropyl.

In another embodiment, $R^1$, $R^2$ and/or $R^3$ is butyl. $R^1$, $R^2$ and/or $R^3$ may be n-butyl, sec-butyl, isobutyl or tert-butyl. In a particular embodiment, $R^1$, $R^2$ and/or $R^3$ is tert-butyl.

In another embodiment, $R^1$, $R^2$ and/or $R^3$ is pentyl. $R^1$, $R^2$ and/or $R^3$ may be straight-chained (n-pentyl) or branched (e.g., neopentyl or isopentyl). In a particular embodiment, $R^1$, $R^2$ and/or $R^3$ is neopentyl. In another particular embodiment, $R^1$ or $R^2$ is neopentyl.

In another embodiment, $R^1$, $R^2$ and/or $R^3$ is hexyl.
In another embodiment, $R^1$, $R^2$ and/or $R^3$ is heptyl.
In another embodiment, $R^1$, $R^2$ and/or $R^3$ is octyl.

As used herein, the variables, x, y and z are used to represent how many particular R substituents are attached to the appropriate carbon.

In one embodiment, x and z are independently zero, 1 or 2.
In one embodiment, y is zero or 1.
In a particular embodiment, x is one and y and z are each zero.

In another particular embodiment, y is one, and x and z are each zero.

In another particular embodiment, at least two of x, y and z are one.

In another particular embodiment, x, y and z are each one.

In a particular embodiment, the complex according to Formula IA is

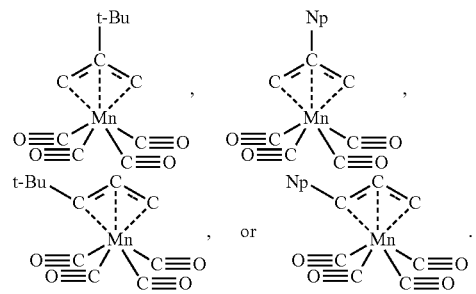

In another embodiment, an organometallic complex is provided represented by Formula II:

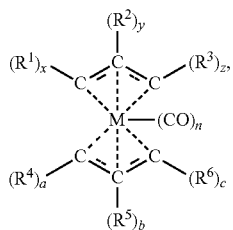

(Formula II)

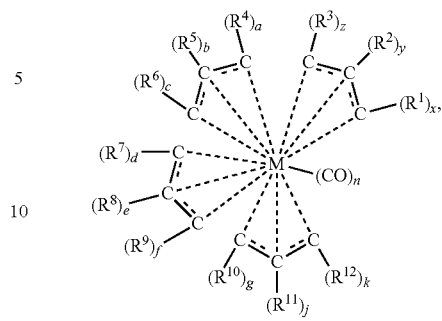

(Formula IV)

wherein
M is Ti, Cr, Fe or Ni;
$R^1$, $R^2$, $R^3$, $R^4$, $R^5$, and $R^6$ are independently $C_1$-$C_8$-alkyl;
x, z, a, and c are independently zero, 1, or 2;
y and b are independently zero or 1; and wherein
when M is Ni, then n is zero;
when M is Fe, then n is 2;
when M is Cr, then n is 3; and
when M is Ti, then n is 4.

In a particular embodiment, the organometallic complex according to Formula II is $Ti(allyl)_2(CO)_4$, $Cr(allyl)_2(CO)_3$, $Fe(allyl)_2(CO)_2$, or $Ni(allyl)_2$.

In another embodiment, an organometallic complex is provided represented Formula III:

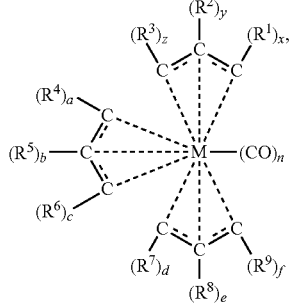

(Formula III)

wherein
M is Mn or V;
$R^1$, $R^2$, $R^3$, $R^4$, $R^5$, $R^6$, $R^7$, $R^8$, and $R^9$ are independently $C_1$-$C_8$-alkyl;
x, z, a, c, d, and f are independently zero, 1, or 2;
y, b, and e are independently zero or 1; and wherein
when M is Mn, then n is 1; and
when M is V, then n is 2.

In a particular embodiment, the organometallic complex according to Formula III is $V(allyl)_3(CO)_2$ or $Mn(allyl)_3(CO)$.

In another embodiment, an organometallic complex is provided represented by Formula IV:

wherein
M is Cr or Ti;
$R^1$, $R^2$, $R^3$, $R^4$, $R^5$, $R^6$, $R^7$, $R^8$, $R^9$, $R^{10}$, $R^{11}$, and $R^{12}$ are independently $C_1$-$C_8$-alkyl;
x, z, a, c, d, f, g, and k are independently zero, 1, or 2;
y, b, e, and j are independently zero or 1; and wherein
when M is Cr, then n is zero; and
when M is V, then n is 1.

In a particular embodiment, the organometallic complex according to Formula IV is $Ti(allyl)_4(CO)$ or $Cr(allyl)_4$.

In another embodiment, an organometallic complex is provided represented by Formula V:

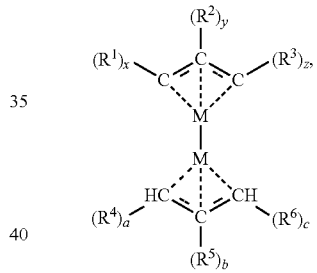

(Formula V)

wherein
M is Ni, Fe, Cr, or Ti;
$R^1$, $R^2$, $R^3$, $R^4$, $R^5$, and $R^6$ are independently $C_1$-$C_8$-alkyl;
x, z, a, and c are independently zero, 1, or 2;
y and b are independently zero or 1; and wherein
when M is Ni, then n is 2;
when M is Fe, then n is 3;
when M is Cr, then n is 4; and
when M is Ti, then n is 5.

In a particular embodiment, the organometallic complex according to Formula V is $Ti_2(allyl)_2(CO)_{10}$, $Cr_2(allyl)_2(CO)_8$, $Fe_2(allyl)_2(CO)_6$, or $Ni_2(allyl)_2(CO)_4$.

In another embodiment, an organometallic complex is provided represented by Formula VI:

$M(CO)_n$ (Formula VI), wherein
M is Fe, Cr, Ti, and Ni; and wherein
when M is Ni, then n is 4;
when M is Fe, then n is 5;
when M is Cr, then n is 6; and
when M is Ti, then n is 7.

In a particular embodiment, the organometallic complex according to Formula VI is $Ti(CO)_7$, $Cr(CO)_6$, $Fe(CO)_5$, or $Ni(CO)_4$.

In another embodiment a method of forming a metal-containing film by a vapor deposition process is provided. The method comprises using at least one complex represented by any of the Formulas disclosed herein. For example, this may include (1) vaporizing the at least one complex and (2) delivering the at least one complex to a substrate surface or passing the at least one complex over a substrate (and/or decomposing the at least one complex on the substrate surface).

In a particular embodiment, the complex may be dissolved in an appropriate solvent such as a hydrocarbon or an amine solvent. Appropriate hydrocarbon solvents include, but are not limited to, aliphatic hydrocarbons, such as hexane, heptane and nonane; aromatic hydrocarbons, such as toluene and xylene; aliphatic and cyclic ethers, such as diglyme, triglyme and tetraglyme. Examples of appropriate amine solvents include, without limitation, octylamine and N,N-dimethyl-dodecylamine. For example, the complex may be dissolved in toluene to yield a 0.05 to 1 M solution.

In one embodiment, the vapor deposition process is chemical vapor deposition.

In another embodiment, the vapor deposition process is atomic layer deposition.

The ALD and CVD methods of the invention encompass various types of ALD and CVD processes such as, but not limited to, conventional processes, liquid injection processes, photo-assisted processes, plasma-assisted, and plasma-enhanced processes.

In one embodiment, conventional (pulsed) CVD is used to form a metal-containing thin film using at least one complex according to any of the Formulas disclosed herein. For conventional CVD processes, see for example Smith, Donald (1995). *Thin-Film Deposition: Principles and Practice*. McGraw-Hill.

In another embodiment, liquid injection CVD is used to form a metal-containing thin film using at least one complex according to any of the Formulas disclosed herein.

Examples of liquid injection CVD growth conditions include, but are not limited to:

(1) Substrate temperature: 100-600° C. on Si(100)
(2) Evaporator temperature: 100-200° C.
(3) Reactor pressure: 1-100 mbar
(4) Solvent: toluene, or any solvent mentioned above
(5) Solution concentration: 0.05-0.2 M
(6) Injection rate: 10-50 $cm^3$ $hr^{-1}$
(7) Argon flow rate: 100-300 $cm^3$ $min^{-1}$
(8) Oxygen flow rate: 0-200 $cm^3$ $min^{-1}$
(9) Hydrogen flow rate: 0-200 $cm^3$ $min^{-1}$
(10) Run time: 5-30 min In another embodiment, photo-assisted CVD is used to form a metal-containing thin film using at least one complex according to any of the Formulas disclosed herein.

In a further embodiment, conventional ALD is used to form a metal-containing thin film using at least one complex according to any of the Formulas disclosed herein. For conventional and/or pulsed injection ALD processes see, for example, George S. M., et al. *J. Phys. Chem.* 100:13121-13131 (1996).

In another embodiment, liquid injection ALD is used to form a metal-containing thin film using at least one complex according to any of the Formulas disclosed herein, wherein at least one liquid complex is delivered to the reaction chamber by direct liquid injection as opposed to vapor draw by a bubbler. For liquid injection ALD processes see, for example, Potter R. J., et al. *Chem. Vap. Deposition*. 11(3):159 (2005).

Examples of liquid injection ALD growth conditions include, but are not limited to:

(1) Substrate temperature: 50-300° C.
(2) Evaporator temperature: 100-200° C.
(3) Reactor pressure: 1-100 mbar
(4) Solvent: toluene, or any solvent mentioned above
(5) Solution concentration: 0.05-0.2 M
(6) Injection rate: about 2.5 µL $pulse^{-1}$ (4 pulses $cycle^{-1}$)
(7) Inert gas flow rate: 100-300 $cm^3$ $min^{-1}$
(8) Reactive gas flow rate: 0-200 $cm^3$ $min^{-1}$
(9) Pulse sequence (sec) (complex/purge/reactive gas/purge): will vary according to chamber size.
(10) Number of cycles: will vary according to desired film thickness.

In another embodiment, photo-assisted ALD is used to form a metal-containing thin film using at least one complex according to any of the Formulas disclosed herein. For photo-assisted ALD processes see, for example, U.S. Pat. No. 4,581,249.

In another embodiment, plasma-assisted ALD is used to form a metal-containing thin film using at least one complex according any of to the Formulas disclosed herein.

Thus, the organometallic complexes according any of to the Formulas disclosed herein utilized in these methods may be liquid, solid, or gaseous. Particularly, the complexes are liquid at ambient temperatures with high vapor pressure allowing for consistent transport of the vapor to the process chamber.

In one embodiment, the complexes represented by the Formulas disclosed herein are delivered to the substrate in pulses alternating with pulses of an oxygen source, such as a reactive oxygen species. Examples of such oxygen source include, without limitation, $H_2O$, $H_2O_2$, $O_2$ and/or ozone.

In one embodiment a manganese-containing film is formed.

In another embodiment, a manganese-oxide film is formed.

In another embodiment, a manganese-nitride film is formed.

In another embodiment, a MnSi film is formed.

In another embodiment, two or more complexes represented by the Formulas disclosed herein may be used to form a thin film.

In another embodiment a "mixed" metal thin film is formed. This method comprises using at least one "co-complex" to form a "mixed" metal film. As used herein, a mixed-metal film contains at least two different metals.

In a particular embodiment, the complexes represented by the Formulas disclosed herein may be used in CVD or ALD with at least one different metal complex to form a mixed-metal film, such as a manganese-tantalum film, a manganese-silicon film, a manganese-iron film, etc.

In a particular embodiment a mixed-metal oxide thin film is formed, such as a manganese-silicon oxide thin film.

In a particular embodiment a mixed-metal nitride thin film is formed, such as a manganese-silicon nitride thin film.

A dielectric film can also be formed by the at least one complex represented by the Formulas disclosed herein, independently or in combination with a co-reactant. In this regard, the co-reactant may be deposited or delivered to or passed over a substrate, independently or in combination with the at least one complex. Examples of such co-reactants include, but are not limited to, hydrogen, hydrogen plasma, oxygen, air, water, $H_2O_2$, ammonia, hydrazine, an alkyl-substituted hydrazine, a borane, a silane, ozone or any combination thereof.

In a particular embodiment, a co-reactant such as hydrazine or an alkyl-substituted hydrazine is used to form a film using at least one complex represented by the Formulas disclosed herein. For example, N,N-dimethylhydrazine (DMHz), tert-butylhydrazine and/or trisilane may be used as a co-reactant.

A variety of substrates can be used in the methods of the present invention to support thin films. For example, the complexes according to any of the Formulas disclosed herein may be delivered for deposition to substrates such as, but not limited to, silicon, silicon oxide, silicon nitride, tantalum, tantalum nitride, copper, ruthenium, titanium nitride, tungsten, and tungsten nitride.

In one embodiment, the method is used for applications such as dynamic random access memory (DRAM) and complementary metal oxide semi-conductor (CMOS) for memory and logic applications on, for example, silicon chips.

In one embodiment, the method provides a film which prevents or resists migration of copper (e.g., copper atoms) through the film to an underlying substrate, for example a silicon dioxide substrate. In this regard, the film provided may be considered a barrier film.

Fundamental differences exist between the thermally-driven CVD process and the reactivity-driven ALD process. The requirements for complex properties to achieve optimum performance vary greatly. In CVD a clean thermal decomposition of the complex to deposit the required species onto the substrate is critical. However, in ALD such a thermal decomposition is to be avoided at all costs. In ALD the reaction between the input reagents must be rapid and result in the target material formation on the substrate. However, in CVD any such reaction between species is detrimental due to their gas phase mixing before reaching the substrate to generate particles. In general it is accepted that a good CVD source will be a poorer ALD source and vice versa and therefore it is surprising that the substituted-allyl complexes of this invention perform well in both ALD and CVD processes albeit under different process conditions.

The substituted-allyl complexes offer access to different temperature windows for deposition processes when compared to conventional precursors. This makes matching of these substituted-allyl complexes with other metal sources open to more manipulation when attempting to deposit ternary or quaternary alloys in an optimized fashion.

The present invention, thus generally described, will be understood more readily by reference to the following examples, which is provided by way of illustration and is not intended to be limiting.

EXAMPLES

The following examples are merely illustrative, and do not limit this disclosure in any way.

Conventional synthesis processes use $Et_2O$ as solvent. Raw materials/intermediates are not very soluble in $Et_2O$ and thus need large amounts of solvent. Alternative solvents in which these materials are more soluble, for example THF (tetrahydrofuran)-$Me_2O$, are better for scale up and reduction in chemical volumes needed.

Example 1

Preparation of $Mn(\eta^3$-2-tert-butylallyl$)(CO)_4$

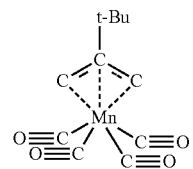

A. Preparation of $K[Mn(CO)_5]$.

A pale-yellow solution of $Mn_2(CO)_{10}$ (20.0 g, 0.051 mol) in THF (~600 mL) was cooled to 0° C. and NaK (10 mL) was added. The solution was stirred for 6 hours and then overnight. On stifling vigorously overnight, a green solution with a dark suspension was obtained. Quenching a small sample with methyl iodide (MeI) confirmed complete conversion to $KMn(CO)_5$. The solution was filtered through a small plug of celite and approximately half the volume of THF removed in vacuo.

B. Preparation of $Mn(\eta^1$-2-tert-butylallyl$)(CO)_5$.

The THF solution of $K[Mn(CO)_5]$ (0.103 mol) was cooled using dry ice and tert-butylallyl bromide (i.e., 2-bromomethyl-3,3-dimethylbut-ene, 18.2 g, 15.1 mL, 0.103 mol) was syringed in. There was an immediate reaction and the solution turned orange. The dry ice was removed from around the reaction mixture and the reaction stirred overnight, by which time it was light orange with a white precipitate. An infrared spectrum showed that the product was essentially $Mn(\eta^1$-2-tert-butylallyl$)(CO)_5$ with virtually nothing else present. The solution was reduced to an oily solid on the rotavap and the solid extracted into ~300 mL of hexane and filtered.

C. Preparation of $Mn(\eta^3$-2-tert-butylallyl$)(CO)_4$.

The filtered solution containing $Mn(\eta^1$-2-tert-butyllallyl$)(CO)_5$ was pumped through an UV lamp using a liquid pump for 3-6 hours to convert the $\eta^1$ complex to $\eta^3$ complex. The solvent was removed in vacuo and the liquid transferred into a 250 mL flask. Distillation up a 10 cm B14 Vigreux column gave 9.97 g (50%) of a yellow/brown fraction starting at 62-64° C. at 0.4 mmHg.

NMR ($C_6D_6$) $^1H$; 0.92 (s, 9H, tert-Bu), 1.19 (s, 2H, $H_{anti}$), 2.37 (s, 2H, $H_{syn}$), $^{13}C\{^1H\}$ 30.2 (s, tert-Bu), 36.5 (s, C tert-Bu), 37.0 (s, $CH_2$), 219.9, 218.3, 214.8 (s, br, CO).

IR ($cm^{-1}$, in cyclohexane): 2065(m), 1993(m), 1960(s), 1926(w).

FIG. 1 shows a TGA plot of $Mn(\eta^3$-2-tert-butylallyl$)(CO)_4$ in comparison to that of $Mn(\eta^3$-allyl$)(CO)_4$ with a temperature ramp from RT to ~400° C. $Mn(\eta^3$-allyl$)(CO)_4$ was prepared in a similar manner to $Mn(\eta^3$-2-tert-butylallyl$)(CO)_4$, using allyl bromide instead of tert-butylallyl bromide (see, for example, McClellan W. R. et al. *J. Am. Chem. Soc.* 83:1601-1607 (1961)).

Example 2

Preparation of Mn($\eta^3$-2-neopentylallyl)(CO)$_4$

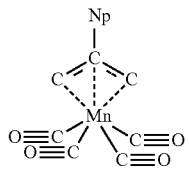

Mn($\eta^3$-2-neopentylallyl)(CO)$_4$ may be prepared in a similar manner to Mn($\eta^3$-2-tert-butylallyl)(CO)$_4$, using neopentylallyl bromide instead of tert-butylallyl bromide.

Example 3

CVD Studies

In general, conventional, pulsed CVD experiments were carried out using a homemade tool fitted with a bubbling/vapor draw precursor inlet system. For CVD experiments targeting pure metal, nitrogen gas was employed as the carrier/purge gas. Mn($\eta^3$-2-tert-butylallyl)(CO)$_4$ was used as the precursor. Mn($\eta^3$-2-neopentylallyl)(CO)$_4$, Mn($\eta^3$-allyl)(CO)$_4$, and other Mn($\eta^3$-alkylallyl)(CO)$_4$ derivatives may similarly be used to prepare Mn-containing films.

Example 3a

CVD with No Co-Reactant

Films were deposited on hydrogen terminated silicon, tantalum nitride, ruthenium, or thermal silicon oxide using neat precursor.

CVD of the precursor (40° C.) was performed using bubbler delivery. Runs were done with a substrate temperature of 200° C. and 500 cycles with no co-reactant. Additional parameters are shown in Table 2, below.

TABLE 2

| CVD Growth Conditions with No Co-reactant | |
|---|---|
| Ampoule (precursor) temperature | 40° C. |
| Substrate temperature(s) | 200° C. |
| Carrier gas | 0 to 100 sccm N$_2$ |
| Temperature of lines to chamber | 60° C. |
| Purge gas | 100 sccm N$_2$ |
| Base pressure during run | 500 mtorr |
| Pulse sequence | 2.0 sec every 7.0 sec |

Table 3, below, shows the composition of film (atomic %) deposited by the parameters listed in Example 3a, as determined by XPS analysis. The surface was sputtered with argon ions for 0 sec, 30 sec, 1.5 min, 3 min, and 5 min. Within the film (>30 min sputter time), the carbon levels are very low. The high O content within the film is presumably caused by post deposition exposure to air.

TABLE 3

| | Si 2p | C 1s | O 1s | Mn 2p |
|---|---|---|---|---|
| 0 sec | 0 | 36 | 42 | 21 |
| 30 sec | 0 | 4.5 | 42 | 53 |

TABLE 3-continued

| | Si 2p | C 1s | O 1s | Mn 2p |
|---|---|---|---|---|
| 1.5 min | 0 | 2.4 | 42 | 55 |
| 3 min | 0 | 2 | 41 | 56 |
| 5 min | 0 | 1.8 | 40 | 58 |

Figure 2:
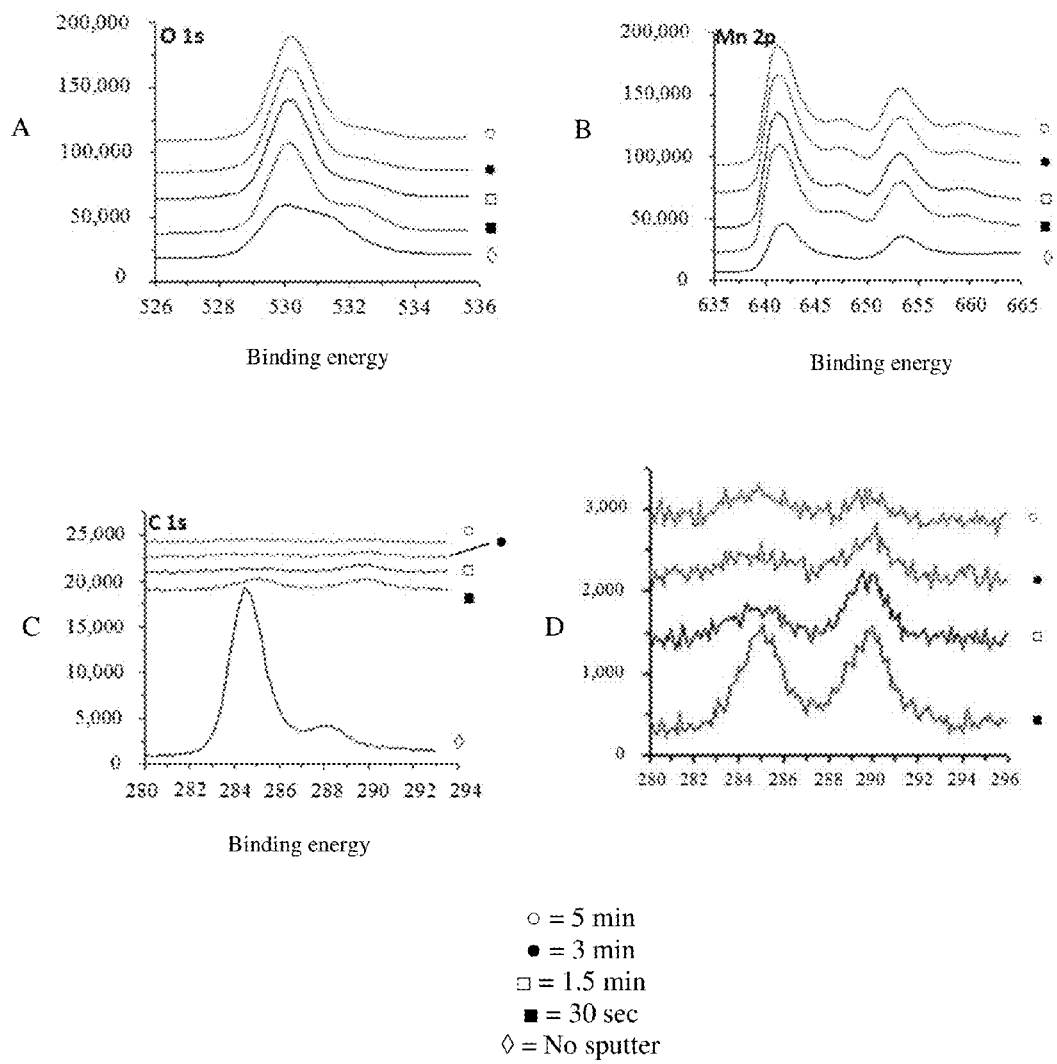
FIG. 2 is a graphical representation of X-ray photoelectron spectroscopy (XPS) data of a film deposited by CVD on $SiO_2$. The film was prepared using $Mn(\eta^3\text{-}2\text{-tert-butylallyl})(CO)_4$ as the manganese precursor.

FIG. 2 is a graphical representation of XPS data of a film deposited on silicon dioxide by the parameters listed in Example 3a. The spectra show ionizations belonging to O 1s (FIG. 2A), Mn 2p (FIG. 2B), and C 1s (FIG. 2C with expansion shown in FIG. 2D) at different sputtering intervals from 0-5 minutes. The oxygen is likely being incorporated by post deposition exposure to air.

Example 3b

CVD with N,N-Dimethylhydrazine Co-Reactant

Films were deposited on silicon with native oxide, tantalum nitride or thermal silicon oxide using neat precursor.

CVD of the precursor (50° C.) was performed using vapor draw delivery. Runs were done with a substrate temperature of 140° C. and 500 cycles with N,N-dimethylhydrazine as co-reactant. Additional parameters are shown in Table 4 below.

TABLE 4

| CVD Growth Conditions with N,N-Dimethylhydrazine Co-reactant | |
|---|---|
| Ampoule (precursor) temperature | 50° C. |
| Substrate temperature(s) | 140° C. |
| Carrier gas | 0 to 100 sccm N$_2$ |
| Temperature of lines to chamber | 65° C. |
| Purge gas | 10 sccm N$_2$ |
| Base pressure during run | 100 mtorr |
| Pulse sequence | 0.5 sec pulse every 20 sec |

Example 4

ALD Studies

In general, conventional (pulsed), ALD experiments were carried out using a homemade tool fitted with bubbling/vapor draw precursor inlet system. For ALD experiments targeting pure metal, nitrogen gas was employed as carrier/purge gas. Mn($\eta^3$-2-tert-butylallyl)(CO)$_4$ was used as the precursor. Mn($\eta^3$-2-neopentylallyl)(CO)$_4$, Mn($\eta^3$-allyl)(CO)$_4$, and other Mn($\eta^3$-alkylallyl)(CO)$_4$ derivatives may similarly be used to prepare Mn-containing films.

Example 4a

ALD with Hydrazine Co-Reactant

Films were deposited on hydrogen terminated silicon, tantalum nitride, ruthenium, or thermal silicon oxide using neat precursor.

ALD of the precursor (50° C.) was performed using bubbler delivery. Runs were done with a substrate temperature of 200° C. and 500 cycles with hydrazine as a co-reactant. Additional parameters are shown in Table 5, below.

TABLE 5

ALD Growth Conditions with Hydrazine Co-reactant

| | |
|---|---|
| Ampoule (precursor) temperature | 50° C. |
| Substrate temperature(s) | 200° C. |
| Carrier gas | 0 to 100 sccm $N_2$ |
| Temperature of lines to chamber | 60° C. |
| Purge gas | 100 sccm $N_2$ |
| Base pressure during run | 500 mtorr |
| Mn Precursor pulse | 2.0 sec |
| Hydrazine pulse | 1.0 sec |
| Purge between precursor pulses | 5.0 sec |

Example 4b

ALD with N,N-Dimethylhydrazine Co-Reactant

The ALD experiments targeted pure metal, and nitrogen gas was employed as carrier/purge gas and was employed in the alternating pulse cycle.

Films were deposited on silicon with native $SiO_2$, thermal silicon oxide or tantalum nitride using neat precursor.

ALD of the precursor (50° C.) was performed using vapor draw delivery. Runs were done with a substrate temperature of 150° C. with N,N-dimethylhydrazine as co-reactant.

Additional parameters are shown in Table 6, below.

TABLE 6

ALD Growth Conditions with N,N-Dimethylhydrazine Co-reactant

| | |
|---|---|
| Substrate temperature | 150° C. |
| Number of cycles | 300-1000 |
| Pulse sequence (sec) | |
| [Mn precursor]/purge/[co-reactant]/purge/-- | 0.2 sec/10 sec $N_2$ purge/0.2 sec DMHz/10 sec $N_2$ purge |

Figure 3:
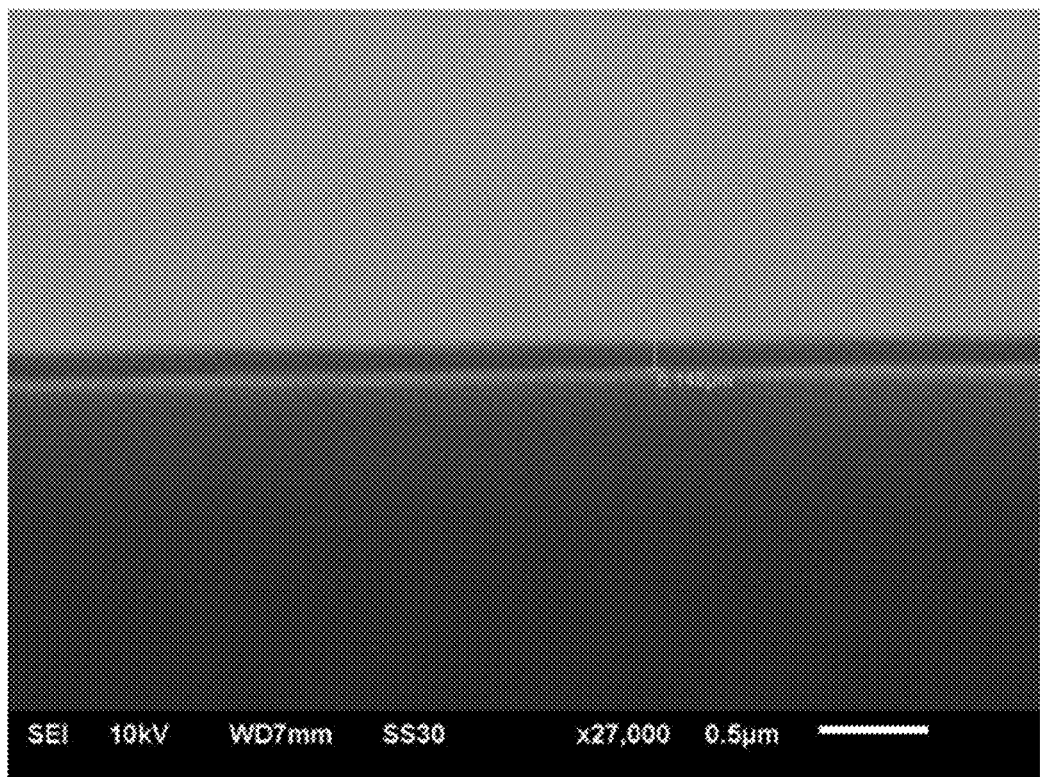
FIG. 3 represents scanning electron microsopy (SEM) of 148 nm of Mn-containing film on tantalum nitride, prepared using $Mn(\eta^3\text{-}2\text{-tert-butylallyl})(CO)_4$ as the manganese precursor. The growth rate was 1.48 Å/cycle.
Figure 4:
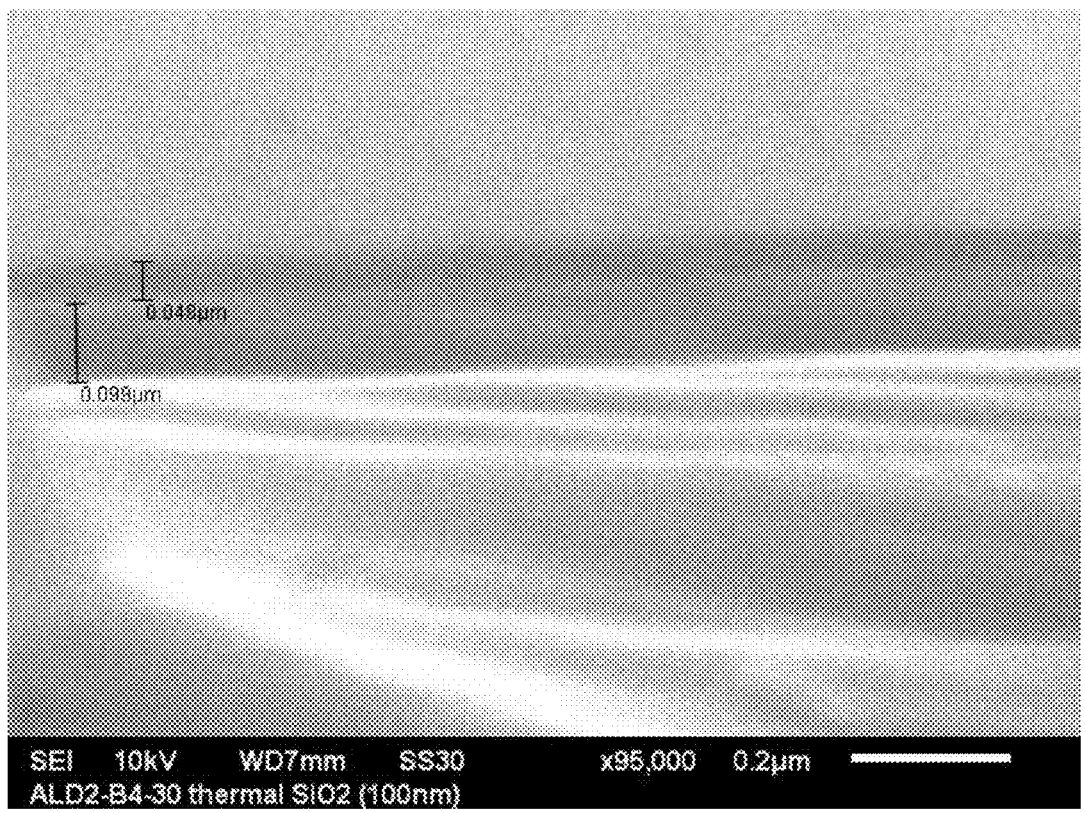
FIG. 4 represents SEM of 48 nm of Mn-containing film on 99 nm of $SiO_2$, prepared using $Mn(\eta^3\text{-}2\text{-tert-butylallyl})(CO)_4$ as the manganese precursor. The growth rate was 0.48 Å/cycle.
Figure 5:
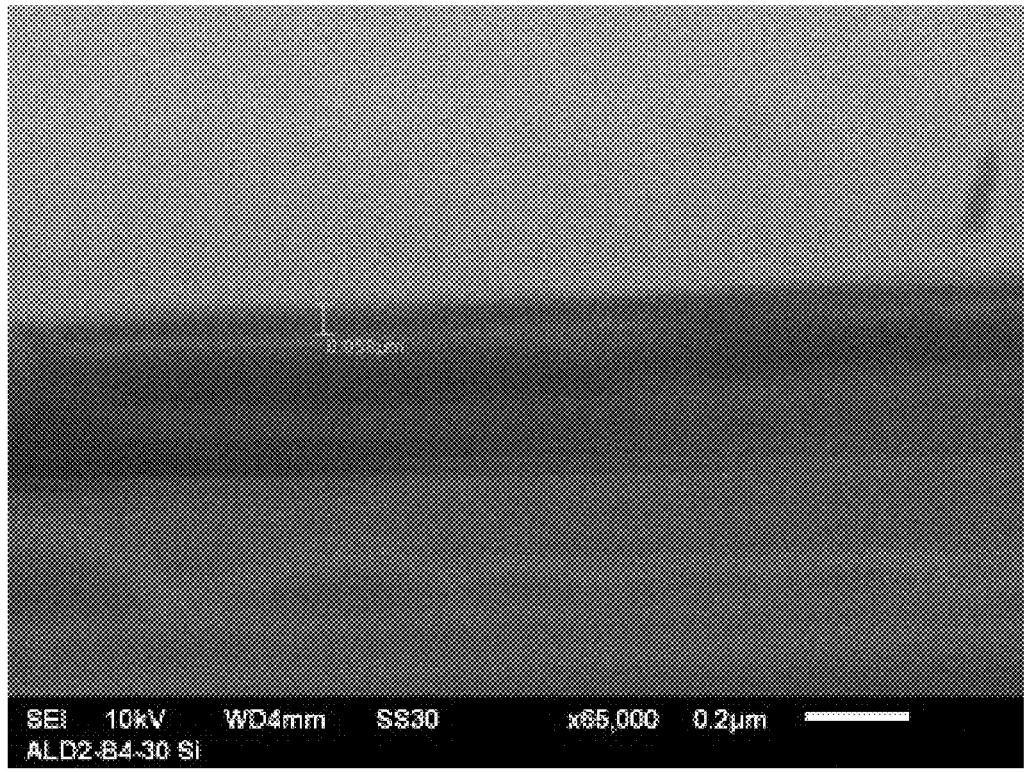
FIG. 5 represents SEM of 58 nm of Mn-containing film on Si(100) native oxide, prepared using $Mn(\eta^3\text{-}2\text{-tert-butylallyl})(CO)_4$ as the manganese precursor. The growth rate was 0.58 Å/cycle.

FIGS. 3-5 show SEM micrographs of Mn-containing films on tantalum nitride (FIG. 3), thermal $SiO_2$ (FIG. 4), and Si(100) native oxide (FIG. 5), obtained from this Example.

Example 5

Plasma Enhanced-ALD (PE-ALD)

PE-ALD experiments were carried out using a homemade tool fitted with bubbling/vapor draw precursor inlet system and a RF plasma generator. For PE-ALD experiments targeting pure metal, nitrogen gas was employed as carrier/purge gas. Hydrogen was used as the plasma gas, at a base pressure of 68 mTorr. The load power for the plasma generator was set to 200 W, with a reflected power of ~7-10 W.

Films were deposited on hydrogen terminated silicon, tantalum nitride, ruthenium, or thermal silicon oxide using neat $Mn(\eta^3$-2-tert-butylallyl)(CO). $Mn(\eta^3$-2-neopentylallyl)$(CO)_4$, $Mn(\eta^3$-allyl)$(CO)_4$, and other $Mn(\eta^3$-alkylallyl)$(CO)_4$ derivatives may similarly be used to prepare Mn-containing films.

PE-ALD of the precursor (50° C.) was performed using bubbler delivery. Runs were done with a substrate temperature of 150° C. and 500 cycles with hydrogen plasma as a co-reactant. Additional parameters are shown in Table 7, below.

TABLE 7

PE-ALD Growth Conditions

| | |
|---|---|
| Ampoule (precursor) temperature | 50° C. |
| Substrate temperature(s) | 150° C. |
| Carrier gas | 0 to 100 sccm $N_2$ |
| Temperature of lines to chamber | 60° C. |
| Purge gas | 40 sccm $N_2$ |
| Base pressure during run | 68 mtorr |
| Mn Precursor pulse | 1.0 sec |
| Hydrogen plasma pulse | 10.0 sec |
| Purge between precursor pulses | 10.0 sec |

When used in combination with hydrazines, such as N,N-dimethylhydrazine or tert-butylhydrazine, ALD growth of manganese film is observed at substrate temperatures of 150° C. Therefore, bulky-substituted allyl precursors, such as $Mn(\eta^3$-2-neopentylallyl)$(CO)_4$ and $Mn(\eta^3$-2-tert-butylallyl)$(CO)_4$ are clearly much better suited to deposition of high quality films using ALD. The ability to perform ALD below the CVD window with $Mn(\eta^3$-2-neopentylallyl)$(CO)_4$ and $Mn(\eta^3$-2-tert-butylallyl)$(CO)_4$ is surprising.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The words "comprise", "comprises", and "comprising" are to be interpreted inclusively rather than exclusively.

What is claimed is:

1. An organometallic complex represented by Formula IA:

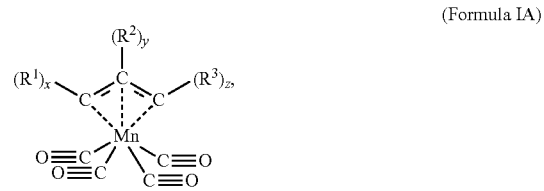

(Formula IA)

wherein
$R^1$, $R^2$, and $R^3$ are independently $C_1$-$C_8$-alkyl;
x and z are independently zero, 1 or 2;
y is zero or 1; and wherein
at least one of $R^1$, $R^2$, or $R^3$ is $C_5$-$C_8$-alkyl.

2. The complex of claim 1, wherein at least one of $R^1$, $R^2$, or $R^3$ is branched $C_5$-$C_8$-alkyl.

3. The complex of claim 1, wherein $R^1$ or $R^2$ is neopentyl.

4. The complex of claim 1, wherein the complex is:

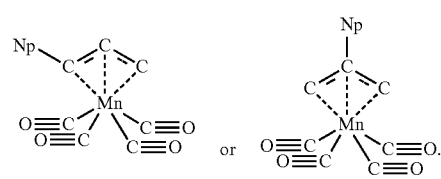

5. A method for forming a metal-containing film by a vapor deposition process, the method comprising delivering to a substrate at least one complex represented by Formula IA:

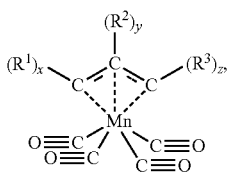

(Formula IA)

wherein
$R^1$, $R^2$, and $R^3$ are independently $C_1$-$C_8$-alkyl;
x and z are independently zero, 1 or 2; and
y is zero or 1.

6. The method of claim 5, wherein x is one; and y and z are each zero.

7. The method of claim 5, wherein y is one; and x and z are each zero.

8. The method of claim 5, wherein at least two of x, y and z are one.

9. The method of claim 5, wherein x, y and z are each one.

10. The method of claim 5, wherein $R^1$, $R^2$, and $R^3$ are independently selected from the group consisting of methyl, ethyl, propyl, isopropyl, butyl, tert-butyl, pentyl, and neopentyl.

11. The method of claim 5, wherein the at least one complex is:

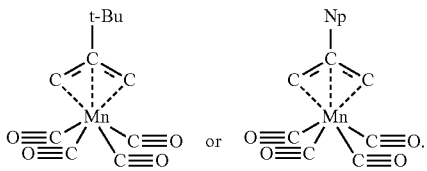

12. The method of claim 5, wherein the at least one complex is:

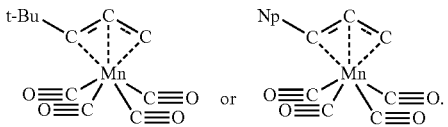

13. The method of claim 5, wherein the vapor deposition process is chemical vapor deposition.

14. The method of claim 13, wherein the chemical vapor deposition is liquid injection chemical vapor deposition.

15. The method of claim 5, wherein the vapor deposition process is atomic layer deposition.

16. The method of claim 15, wherein the atomic layer deposition is selected from the group consisting of liquid injection atomic layer deposition; pulsed injection atomic layer deposition; and plasma-enhanced atomic layer deposition.

17. The method of claim 5, wherein the at least one complex is delivered to the substrate in pulses alternating with pulses of an oxygen source to form a metal oxide film.

18. The method of claim 17, wherein the oxygen source is selected from the group consisting of $H_2O$, $O_2$ and ozone.

19. The method of claim 5, further comprising delivering to the substrate at least one co-complex to form a mixed-metal oxide film.

20. The method of claim 19, wherein the mixed-metal oxide film comprises manganese and silicon.

21. The method of claim 5, further comprising using at least one co-reactant selected from the group consisting of hydrogen, hydrogen plasma, oxygen, air, water, ammonia, hydrazine, an alkyl-substituted hydrazine, a borane, a silane, ozone and a combination thereof.

22. The method of claim 5, further comprising using an alkyl-substituted hydrazine as a co-reactant.

23. The method of claim 22, wherein the alkyl-substituted hydrazine is N,N-dimethylhydrazine.

24. The method of claim 5, wherein the at least one complex is delivered to a substrate selected from the group consisting of silicon, silicon oxide, silicon nitride, tantalum, tantalum nitride, copper, ruthenium, titanium nitride, tungsten, and tungsten nitride.

25. The method of claim 5, wherein the film formed comprises a manganese-nitride thin film.

26. The method of claim 5, wherein the method is used for a DRAM or CMOS application.

* * * * *

UNITED STATES PATENT AND TRADEMARK OFFICE
CERTIFICATE OF CORRECTION

| | | |
|---|---|---|
| PATENT NO. | : 8,927,748 B2 | Page 1 of 1 |
| APPLICATION NO. | : 13/569906 | |
| DATED | : January 6, 2015 | |
| INVENTOR(S) | : Odedra et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 149 days.

Signed and Sealed this
Eleventh Day of August, 2015

Michelle K. Lee
*Director of the United States Patent and Trademark Office*